US012571380B2

(12) United States Patent
Algawi et al.

(10) Patent No.: US 12,571,380 B2
(45) Date of Patent: ***Mar. 10, 2026

(54) USING BALLOON AS DAMPER FOR PORT OF A RECIPROCATING PUMP

(71) Applicant: Biosense Webster (Israel) Ltd., Yokneam (IL)

(72) Inventors: Yehuda Algawi, Binyamina (IL); Assaf Govari, Haifa (IL); Ilya Sitnitsky, Nahariya (IL); Gili Attias, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/372,498

(22) Filed: Sep. 25, 2023

(65) Prior Publication Data

US 2024/0011472 A1 Jan. 11, 2024

Related U.S. Application Data

(62) Division of application No. 16/585,311, filed on Sep. 27, 2019, now Pat. No. 11,767,834.

(60) Provisional application No. 62/786,406, filed on Dec. 29, 2018, provisional application No. 62/786,402, filed on Dec. 29, 2018, provisional application No. 62/786,407, filed on Dec. 29, 2018, provisional application No. 62/786,404, filed on Dec. 29, 2018.

(51) Int. Cl.
    | | |
    |---|---|
    | *F04B 5/02* | (2006.01) |
    | *A61M 5/142* | (2006.01) |
    | *F04B 11/00* | (2006.01) |

(52) U.S. Cl.
CPC ............ *F04B 5/02* (2013.01); *A61M 5/14216* (2013.01); *F04B 11/00* (2013.01); *F04B 11/0008* (2013.01); *A61M 5/1422* (2013.01)

(58) Field of Classification Search
CPC ........ F04B 5/02; F04B 11/00; F04B 11/0008; A61M 5/14216; A61M 5/1422; Y10T 29/49236
See application file for complete search history.

(56) References Cited

U.S. PATENT DOCUMENTS

| | | | |
|---|---|---|---|
| 1,290,803 | A | 1/1919 | Thoens |
| 1,598,137 | A | 8/1926 | Jacobsen |
| 1,625,500 | A | 4/1927 | Quinn |

(Continued)

FOREIGN PATENT DOCUMENTS

| | | |
|---|---|---|
| CN | 2178285 Y | 9/1994 |
| EP | 2061536 B1 | 10/2011 |

(Continued)

OTHER PUBLICATIONS

Chinese First Office Action and Search Report dated Jun. 2, 2023, for Application No. 201911377931.2, 12 pages.

(Continued)

*Primary Examiner* — Charles G Freay
(74) *Attorney, Agent, or Firm* — FBT GIBBONS LLP

(57) ABSTRACT

A disposable single-piston dual-action reciprocating pump part includes a single piston, an output port, and a balloon damper. The output port is configured for outputting fluid pumped by the single piston. The balloon damper is fitted in the output port, and the balloon damper is configured to suppress a pulsation in a flow rate of the outputted fluid.

18 Claims, 4 Drawing Sheets

(56)                    References Cited

U.S. PATENT DOCUMENTS

| | | | |
|---|---|---|---|
| 3,172,369 A * | 3/1965 | Ballu | F04B 53/102 |
| | | | 92/97 |
| 3,771,918 A | 11/1973 | Winter | |
| 3,818,934 A | 6/1974 | Borsanyi | |
| 3,838,941 A * | 10/1974 | Roschupkin | F04B 53/164 |
| | | | 417/276 |
| 4,264,287 A | 4/1981 | Ishida et al. | |
| 4,575,313 A | 3/1986 | Rao et al. | |
| 4,919,888 A * | 4/1990 | Spence | A61L 2/26 |
| | | | 422/26 |
| 5,450,743 A | 9/1995 | Buote | |
| 5,613,420 A | 3/1997 | Glockemann | |
| 5,817,955 A | 10/1998 | Gherson et al. | |
| 5,921,951 A | 7/1999 | Morris | |
| 8,672,653 B2 | 3/2014 | Mancini et al. | |
| 9,107,986 B2 | 8/2015 | Bonnette et al. | |
| 10,011,254 B2 | 7/2018 | Her | |
| 11,767,834 B2 | 9/2023 | Algawi et al. | |
| 2003/0220608 A1 | 11/2003 | Huitt et al. | |
| 2008/0195058 A1 | 8/2008 | Moutafis et al. | |
| 2008/0217245 A1 | 9/2008 | Rambod et al. | |
| 2010/0318025 A1 | 12/2010 | John | |
| 2011/0106003 A1 | 5/2011 | Childers et al. | |
| 2011/0144586 A1 | 6/2011 | Michaud et al. | |
| 2011/0196303 A1 * | 8/2011 | Chan | F04B 11/0008 |
| | | | 604/151 |
| 2012/0053557 A1 | 3/2012 | Abal | |
| 2013/0123689 A1 | 5/2013 | Bosman et al. | |
| 2014/0224829 A1 | 8/2014 | Bazala et al. | |
| 2014/0276379 A1 | 9/2014 | Uram et al. | |
| 2015/0327875 A1 | 11/2015 | Look et al. | |
| 2017/0326282 A1 | 11/2017 | Wilt et al. | |

FOREIGN PATENT DOCUMENTS

| | | |
|---|---|---|
| JP | S50-014169 Y | 5/1975 |
| KR | 101510004 B1 | 4/2015 |
| WO | 2016/033351 A2 | 3/2016 |

OTHER PUBLICATIONS

Chinese Second Office Action dated Oct. 27, 2023, for Application No. 201911377931.2, 13 pages.

Chinese Final Office Action dated Apr. 2, 2024, for Application No. 201911377931.2, 14 pages.

European Extended Search Report and Written Opinion dated Apr. 20, 2020, for Application No. 19220214.1, 8 pages.

European Communication dated Mar. 17, 2023, for Application No. 19220214.1, 6 pages.

Japanese Office Action Dated Sep. 5, 2023, for Application No. 2019-235848, 2 pages.

\* cited by examiner

USING BALLOON AS DAMPER FOR PORT OF A RECIPROCATING PUMP

CROSS-REFERENCE TO RELATED APPLICATIONS

This application is a divisional of, and claims priority to U.S. patent application Ser. No. 16/585,311, filed Sep. 27, 2019, which claims the benefit of U.S. Provisional Patent Application 62/786,406, filed Dec. 29, 2018, U.S. Provisional Patent Application 62/786,402, filed Dec. 29, 2018, U.S. Provisional Patent Application 62/786,404, filed Dec. 29, 2018, and U.S. Provisional Patent Application 62/786,407, filed Dec. 29, 2018, whose disclosures are incorporated herein by reference.

FIELD OF THE INVENTION

The present invention relates generally to medical pumps, and particularly to single-use medical pumps.

BACKGROUND OF THE INVENTION

Various designs for medical pumps that may be one-time used were proposed in the patent literature. For example, U.S. Patent Application Publication 2008/0195058 describes apparatus and methods for engaging a pumping cartridge with a pump drive. In certain embodiments, the cartridge, comprising a cylinder and a movable piston assembly, is initially assembled or subsequently positioned so that the distance between the attachment point on the piston assembly for coupling to a drive assembly, and a reference point on the cylinder, is greater than the maximal distance that will be encountered during normal oscillation of the piston during use. The cartridge, in certain embodiments may be pressed into a drive assembly having means for immobilizing the cartridge and means for coupling the piston assembly to the driveshaft. In certain embodiments, when the cartridge is fully inserted into the drive assembly, the piston is pressed into the cylinder sufficiently to establish a selected distance so that the piston shaft is in the proper position to engage with a coupling mechanism carried on the driveshaft.

As another example, U.S. Patent Application Publication 2015/0327875 describes a system for aspirating thrombus that includes a catheter having an aspiration lumen configured to couple to a vacuum source. The system further has a disposable tubing set having a first conduit configured to couple the supply lumen of the aspiration catheter to a fluid source, and a pump component associated with the first conduit and configured to detachably couple to a drive unit.

Various designs for controlling an output flow of a medical pump are known in the art. For example, U.S. Patent Application Publication 2013/0123689 describes a breast pump apparatus comprising a vacuum pump and a variable-volume buffer volume coupled together in fluid communication. The apparatus also includes a breast-receiving portion coupled to the vacuum pump and the buffer volume such that the vacuum pump is operable to generate negative pressure at the breast-receiving portion to stimulate milk expression, and the negative pressure generated at the breast-receiving portion can be controlled by controlling the buffer volume.

As another example, U.S. Patent Application Publication 2003/0220608 describes a method, system and apparatus for performing peritoneal dialysis. To this end, in part, a method of controlling pressure in a medical fluid pump is provided. The method includes the steps of controlling a pump member acceleration during a first portion of a pump stroke and adaptively changing the pump member velocity during a second portion of the pump stroke.

U.S. Patent Application Publication 2017/0326282 describes hemodialysis and similar dialysis systems. According to one aspect, a blood pump of the system is configured to pump blood to a dialyzer of a hemodialysis apparatus, wherein the blood pump comprising a pneumatically actuated or controlled reciprocating diaphragm pump. In an embodiment, the diaphragm of the pump comprises a flexible membrane formed or molded to generally conform to a curved inner wall of a pumping chamber or control chamber of the pump, wherein the diaphragm is pre-formed or molded to have a control side taking a convex shape, so that any elastic tension on the diaphragm is minimized when fully extended into a control chamber of the pump.

U.S. Pat. No. 5,921,951 describes an apparatus for pumping fluid at a steady rate. A first drive chamber having a movable outer surface, and a second drive chamber having a movable outer surface are provided. The apparatus further includes a block having a plurality of internal passages including a first passage for receiving the fluid into the block and a second passage for discharging the fluid from the block at the steady rate. The block has first and second internal chambers which are in fluid connection with the first and second passages. The first internal chamber has a first flexible surface for mating with the movable outer surface of the first drive chamber, and the second internal chamber has a second flexible surface for mating with the movable outer surface of the second drive chamber. At least one actuator is provided for applying positive pressure to the first flexible surface while simultaneously applying negative pressure to the second flexible surface and for applying negative pressure to the first flexible surface while simultaneously applying positive pressure to the second flexible surface. The actuator is respectively coupled to the first and second flexible surfaces by the first and second drive chambers.

U.S. Pat. No. 3,771,918 describes a multiple stage, linear, reciprocating, balanced-unopposed compressor that is driven by an analog of a turnbuckle with the drive having first and second pairs of associated recirculating ball bearing nuts and screws. The ball bearing nuts are constrained against axial displacement and are driven by a source of rotary power. The pairs of recirculating ball bearing nuts and screws are oppositely threaded and the screws are coupled together for reciprocation together. The screws are successively braked to produce reciprocation. The screw under power compresses gas in a plurality of stages in an isomer by driving a plurality of pistons. When the power stroke of a screw is completed, its brake is released and the other screw braked to compress gas in a second isomer identical with the first. The stroke of the compressor is variable for warmup purposes.

Various types of sealing elements for use in a medical pump were proposed in the patent literature. For example, U.S. Patent Application Publication 2014/0224829 describes a fluid pump device that is operable by a drive and actuating system. The fluid pump device includes a pump manifold, a plurality of pump cylinders, a plunger reciprocally operable in each of the pump cylinders, and at least one inlet selector valve. The inlet selector valve may be located laterally outboard of the pump cylinders and extend generally parallel to the pump cylinders. In an embodiment, O-ring seals may be made of any type of suitable elastomeric material including polyurethane, silicone or EPDM rubbers, depending, for example, whether the sealed parts are static or are moving one with respect to the other.

As another example, U.S. Patent Application Publication 2011/0144586 describes portable infusion devices, systems, and methods of using the same for dispensing materials. In some cases, the devices, systems and methods may be used for infusing a material such as medicament, e.g., insulin, into a body in need thereof. In some instances, the seals used may be made from materials such as butyl, silicone, polyurethanes or the like having a shore hardness of about 70 A.

U.S. Patent Application Publication 2011/0106003 describes a peritoneal dialysis system that includes a disposable cassette having an interface that includes at least one pump aperture. An at least one piston head moveable out of and retractable into the at least one pump aperture to move a corresponding pumping portion of a flexible sheet of the disposable cassette, the piston head moving within a vacuum chamber, the vacuum chamber enabling a vacuum to be pulled around the piston head to the flexible sheet of the disposable cassette. In an embodiment, a shaft seal, which can be of any known type, hereafter referred to as an O-ring, is also placed within a housing between a shaft opening and the piston to maintain the vacuum within the chamber.

SUMMARY OF THE INVENTION

An embodiment of the present invention provides a pump device including a rotary motor, a compartment for insertion of a disposable pump part, and one or more pulsation-reduction elements. The disposable pump part includes an input port, an output port, and a dual-action reciprocating assembly. The input port is configured for intaking fluid. The output port is configured for outputting the fluid. The dual-action reciprocating assembly is configured for pumping the fluid, wherein the assembly comprises a single piston and a rod configured to be coupled to the rotary motor, so as to drive the piston. The one or more pulsation-reduction elements are configured to reduce a pulsation in the outputted fluid, caused by the single-piston dual-action reciprocating assembly.

In some embodiments, the one or more pulsation-reduction elements are configured to reduce variations in motion speed of the single piston.

In some embodiments, the one or more pulsation-reduction elements include a balloon damper which is fitted in the output port of the pump part.

In an embodiment, the one or more pulsation-reduction elements include a mechanical smoothing mechanism comprising a guide channel (e.g., a slit) and a bar that are configured to couple a shaft of the rotary motor to the rod, wherein the bar is coupled to the shaft to move rotationally in the guide channel, and wherein a profile of the guide channel is configured to speed-up and a slow-down a reciprocating motion of the rod by rotational motion the of the bar.

In another embodiment, the one or more pulsation-reduction elements include a processor that is configured to vary a rotation speed of the rotary motor.

There is additionally provided, in accordance with an embodiment of the present invention, a disposable pump part for inserting into a compartment of a pump device, the disposable pump part including an input port, an output port, and a single-piston dual-action reciprocating assembly.

The input port is configured for intaking fluid. The output port is configured for outputting the fluid. The dual-action reciprocating assembly is configured for pumping the fluid, wherein the assembly comprises a single piston, non-return valves, a rod, and a mechanical pulsation-reduction element. The non-return valves are configured to open and close interchangeably in response to the pumping by the single piston, so as to provide dual-action reciprocating pumping. The rod is configured to be coupled to a rotary motor of the pump device, so as to drive the single piston. The mechanical pulsation-reduction element is configured to reduce a pulsation in the outputted fluid, caused by the single-piston.

In some embodiments, the input port, the output port and the assembly are configured to be fitted in the pump device, and subsequently removed from the pump device at the end of use.

There is further provided, in accordance with an embodiment of the present invention, a manufacturing method, including assembling a single-use pump part including (a) an input port for intaking fluid, (b) an output port for outputting the fluid, and (c) a single-piston dual-action reciprocating assembly for pumping the fluid, wherein the assembly includes (i) non-return valves, configured to open and close interchangeably in response to the pumping to provide dual-action reciprocating pumping, (ii) a rod configured to be coupled to a rotary motor, so as to drive the dual-action reciprocating assembly, and (iii) one or more pulsation-reduction elements that are configured to reduce a pulsation in the outputted fluid, caused by the single-piston dual-action reciprocating assembly. The assembled pump part is packaged in a sterile package.

There is furthermore provided, in accordance with an embodiment of the present invention, a manufacturing method, including inserting a disposable single-piston dual-action reciprocating pump part into a compartment of a pump device, wherein the pump part includes one or more pulsation-reduction elements that are configured to reduce a pulsation in fluid outputted from the pump part, caused by the single-piston dual-action reciprocating assembly. An input port of the pump part is connected to a fluid supply. An output port is connected to a fluid supply line of a medical device. The pump device is operated from a control panel of the pump device.

Another embodiment of the present invention provides a disposable single-piston dual-action reciprocating pump part that includes a single piston, an output port, and a balloon damper. The output port is configured for outputting fluid pumped by the single piston. The balloon damper is fitted in the output port, wherein the balloon damper is configured to suppress a pulsation in a flow rate of the outputted fluid.

In some embodiments, the balloon damper is configured to accept a shape of a chamber into which the balloon is fitted.

In some embodiments, the balloon damper is configured to suppress the pulsation in the flow rate of the outputted fluid by the balloon damper returning, when the output flow rate is reduced, to an uncompressed volume and pushing extra fluid through the output port.

There is additionally provided, in accordance with an embodiment of the present invention, a manufacturing method including partially assembling a disposable dual-action reciprocating pump part having an output port for outputting fluid. A balloon damper is fitted in the output port, wherein the balloon damper is configured to suppress a pulsation in a flow rate of the outputted fluid, the pump part assembly is then completed.

In some embodiments, the manufacturing method further includes packaging the assembled pump part in a sterile package.

Another embodiment of the present invention provides a disposable dual-action reciprocating pump part that includes an input port, an output port, a single-piston dual-action reciprocating assembly for pumping the fluid, and a mechanical smoothing mechanism. The input port is configured for intaking fluid. The output port is configured for outputting fluid pumped by the single piston. The single-piston dual-action reciprocating assembly for pumping the fluid includes a single piston, and a rod configured to be coupled to a shaft of a rotary motor. The mechanical smoothing mechanism includes a guide channel and a bar, which couples the shaft of the rotary motor to the rod such that a profile of the guide channel, in which the bar moves rotationally, is configured to speed-up and slow-down a reciprocating motion of the rod by rotational motion the of the bar.

In some embodiments, the pump part further includes non-return valves, configured to open and close interchangeably in response to pumping by the single piston, so as to provide dual-action reciprocating pumping.

In some embodiments, the pump part further includes a balloon damper, which is fitted in the output port, wherein the balloon damper is configured to suppress a pulsation in a flow rate at of the outputted fluid.

In some embodiments, the pump part further includes multiple silicone O-rings, which are configured to seal the piston against a cylinder of the pump part.

Another embodiment of the present invention provides a disposable dual-action reciprocating pump part that includes a piston and a cylinder, and multiple silicone O-rings. The piston is configured to move bi-directionally inside the cylinder. The multiple silicone O-rings are configured to seal the piston against the cylinder.

In some embodiments, at least one of the silicone-made is fixed relative to the piston and is configured to slide against the cylinder.

There is further provided, in accordance with an embodiment of the present invention, a manufacturing method, including partially assembling a disposable dual-action reciprocating pump part having a piston and a cylinder, wherein the piston is configured to move bi-directionally inside the cylinder. Multiple silicone made O-rings are fitted, which are configured to seal the piston against the cylinder. The assembly of the pump part in then completed.

In some embodiments, fitting multiple silicone made includes fitting at least one silicone made O-ring over the piston.

The present invention will be more fully understood from the following detailed description of the embodiments thereof, taken together with the drawings in which:

DETAILED DESCRIPTION OF EMBODIMENTS

Overview

Figure 1:
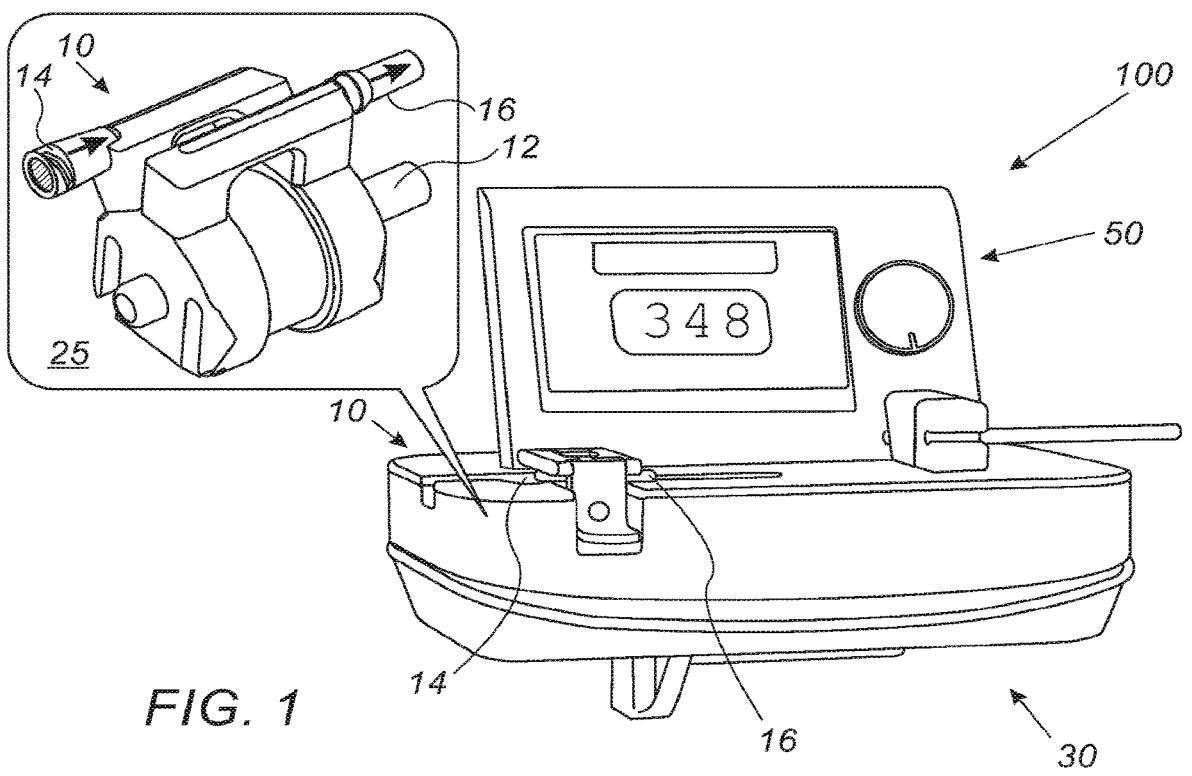
FIG. 1 is a schematic volume rendering of a medical pump device comprising a disposable single-piston dual-action pump part, in accordance with an embodiment of the present invention.

In some medical applications, a disposable medical pump is required to provide an output flow at a constant flow rate. At the same time, such medical pump has to be a low-cost product. While some types of low-cost pumps, such as certain peristaltic pumps, may produce a steady flow, peristaltic pumps typically contain plastic components that are constantly flexed during pumping. The constant flexing of plastic parts generates electrical noise which may be picked up by some medical devices used in a medical procedure and degrade their performance.

Embodiments of the present invention that are described hereinafter provide a disposable single-piston dual-action reciprocating pump part, free of flexing, which includes and/or is coupled to one or more pulsation-reduction elements that are configured to reduce pulsation in the output flow, caused by the reciprocating motion of the single piston of the pump part.

In the context of the disclosed embodiments, pulsation is defined as a periodically recurring alternate increase and decrease of the output flow of the disclosed pump part, which is correlated with the reciprocating motion of the piston. A steady flow of fluid can thus be viewed as a complete lack of pulsation.

The disclosed disposable pump part is configured to be easily fitted (i.e., inserted) in a compartment of a medical pump device (pump device also named hereinafter "pumping system"). The pump part is configured for a "one-off" single use, and is subsequently readily removed from the pump device, e.g., at the end of use. The disposable pump part separates the part of the pump that is in contact with fluid from the pump driver. The entire disposable pump part does not require sterilization before use, and is mostly made of plastics.

In some embodiments, a pump device is provided, which comprise (a) a rotary motor, (b) a compartment for insertion of a disposable pump part, and (c) one or more pulsation-reduction elements included in the pump device. The disposable pump part comprises (i) an input port for intaking fluid, and an output port for outputting the fluid, (ii) a dual-action reciprocating assembly for pumping the fluid, wherein the assembly comprises a single piston and a rod configured to be coupled to the rotary motor, so as to drive the piston.

Examples of pulsation-reduction elements include a damping balloon, a processor, a guide channel of a mechanical smoothing mechanism, the guide channel having a non-linear profile, which are all described below. In general, the disclosed techniques are applicable to any other pulsation-reduction element that operates in conjunction with a single piston pump.

The balloon damper, which is fluid-coupled to the fluid flowing through the output port of the pump part, acts as a smoothing "capacitor" for the output flow. The disclosed balloon damper is fitted into a chamber inside the pump part. When the output flow is reduced the balloon returns to its original uncompressed volume and pushes extra fluid through the output port, thereby reducing the pulsation output to a minimum.

Therefore, the balloon regulates the output flow rate that is modulated by the piston motion by: (i) the balloon being compressed during the constant speed travel section of the piston, and (ii) at the end-points of piston travel, when output pressure falls, the balloon expands, increasing the flow rate from the lower value caused by the piston changing direction. In this solution, the balloon damper is part of an output port of the pump part, all of which are disposable.

The processor element controls the pump motor rotation speed, so that except for the end-points of its travel, the piston travels at a constant speed. At the piston travel end points, the processor varies the rotation speed of the motor to reduce the pulsation.

Alternatively or additionally, the speeding up and slowing down of the piston (i.e., of the rod) is achieved in some embodiments mechanically, utilizing a mechanical smoothing mechanism that the pump device (i.e., pumping system) may comprise. The disclosed mechanical smoothing mechanism couples a rod that is part of the single-use pump part to a shaft of a rotary motor of the pumping device, to convert the rotation of the motor shaft into a periodic variable speed motion of the rod.

To convert motion, the mechanical smoothing mechanism comprises a bar that is coupled to the shaft and is free to move in a guide channel having a non-linear profile. That way, the disclosed smoothing mechanism causes the piston of the pump part, which is fitted on the rod, to accelerate just before reaching travel end-points at which the piston halts. The disclosed piston motion act to compensate for the diminishing flow rate at the piston turning points. In an embodiment, the design of the disclosed mechanical smoothing mechanism further takes into account attenuation of the flow rate along the output path, to provide variable speed piston motion that induces a uniform flow.

Some embodiments of the present invention provide a disposable single-piston dual action reciprocating pump part comprising silicone made O-rings. The silicone made seal the piston against a cylinder, so as to enable pumping fluid as the piston moves bi-directionally inside the cylinder. In some embodiments, at least one of the silicone-made O-rings is fixed relative to the piston and is configured to slide against the cylinder Silicone made O-rings typically exhibit poor tear resistance, abrasion and tensile strength. The poor abrasion resistance of a silicone made O-ring means that such O-ring is generally considered unsuitable for use as a seal with moving parts. In some embodiments of the present invention, however, since the part is intended for "one-off" single use, the silicone made O-ring is also single-use and therefore the above drawbacks do not come into play. Moreover, the velocity of the piston is kept low enough to ensure the silicone O-ring fulfills its task reliably in a "one-off" single use.

Using low cost O-ring in a pump part intended for "one-off" single use may lower the cost of such pump part, and by so increase the adoption of disposable pumps in medical applications such as intravenous infusion of medications.

The disclosed low-cost disposable single-piston dual-action pump with the disclosed techniques for the suppression of output flow pulsation, may be used in medical procedures in which, for example, using a disposable peristaltic pump may introduce electrical disturbances. For example, the disclosed single-use pump part can be used with an irrigated a radiofrequency cardiac ablation catheter, without adding electrical noises to low-amplitude electrophysiological signals sensed by other devices. The disclosed low-cost pump part may therefore increase the adoption of disposable pumps in medical procedures.

System Description

FIG. 1 is a schematic volume rendering of a medical pump device 100 comprising a disposable single-piston dual-action pump part 10, in accordance with an embodiment of the present invention. The entire pump part (part 10) is configured to be easily fitted in device 100 for a single use and readily removed from device 100 at the end of use.

Device 100 further comprises a rotary pump motor 30, which is connected to the pump via a connection mechanism (not marked in the figure) that converts the rotary action of the pump motor into a reciprocating motion of dual-action pump part 10.

Dual-action pump part 10 has a fluid input port 14, to which a fluid supply is connected, and a fluid output port 16, which can be connected, for example, to a fluid supply line of a medical device, such as an irrigation port of a radiofrequency ablation catheter. Device 100 is a stand-alone device operated and monitored from a control panel 50.

Inset 25 shows pump part 10 that is a single part configured to be fitted into device 100. The only interfaces of the part are the fluid input port 14, fluid output port 16, and a moving rod 12 which is coupled to move a piston inside pump part 10 to provide the pumping action.

The example illustration shown in FIG. 1 is chosen purely for the sake of conceptual clarity. Only elements relevant to the invention are described, whereas many other parts included in device 100 are omitted for simplicity. For example, the disclosed single-use pump part 10 is connected to rotary pump motor 30 via a connecting rod and a screw mechanism. The screw mechanism converts the rotary action of the pump motor into a reciprocating motion of the connecting rod.

The example illustration shown in inset 25 is chosen purely for the sake of conceptual clarity. In alternative embodiments, the industrial design of pump part 10 may be different, so as to fit other designs of medical pump device 100.

Disposable Dual Action Reciprocating Pump Assembly

Figure 2:
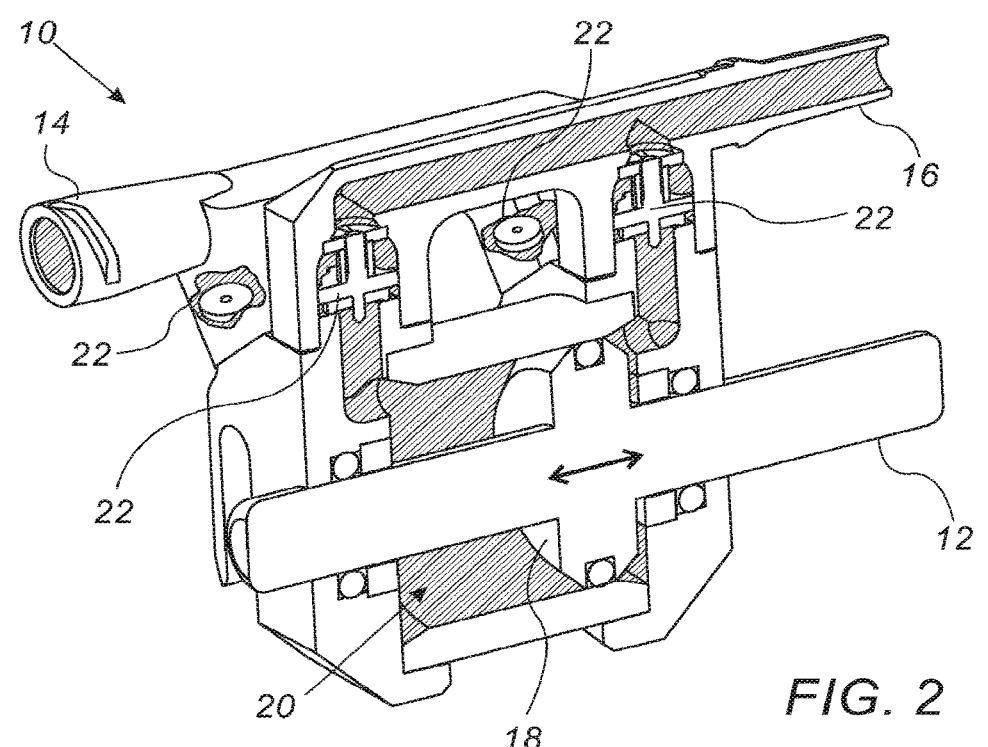
FIG. 2 is a cross-sectional view of the disposable single-piston dual-action pump part of FIG. 1, in accordance with an embodiment of the present invention.

FIG. 2 is a schematic, pictorial illustration of the disposable single-piston dual-action pump part 10 of FIG. 1, in accordance with an embodiment of the present invention. As seen, pumping part 10 is a one-part element that is configured to be fitted into device 100, with the only interfaces of the part being the fluid input port 14, fluid output port 16, and a moving rod 12 which is coupled to move a piston inside pump part 10 to provide the pumping action, as described below.

As seen, rod 12 drives a piston 18 inside a cylinder in a dual direction pumping action. Four non-return valves 22 open and close interchangeably (in pairs) to provide dual-action pumping. The reciprocating motion of piston 18, being usable at both opposing directions, causes fluid to be pumped from input port 14 into output port 16 in a largely continuous flow.

Moreover, by using such a dual-stroke configuration, pump part 10 is capable of pumping fluid largely continuously in a wide range of flow rates, from several ml/min to several tens of ml/min, and in a wide output pressure range, from sub PSI to several tens of PSI.

Pump part 10 is mostly made of low-cost plastics parts, such as non-return valves 22, that allow the one-use model of the disclosed pump device.

The example illustration shown in FIG. 2 is chosen purely for the sake of conceptual clarity. In alternative embodiments, the industrial design of pump part 10 may be different, so as to fit other designs of device 100. Only elements relevant to the invention are described, whereas many other components included in pump part 10, such as O-rings, are not described for simplicity.

Using Balloon as Damper for Port of a Pump

Figure 3:
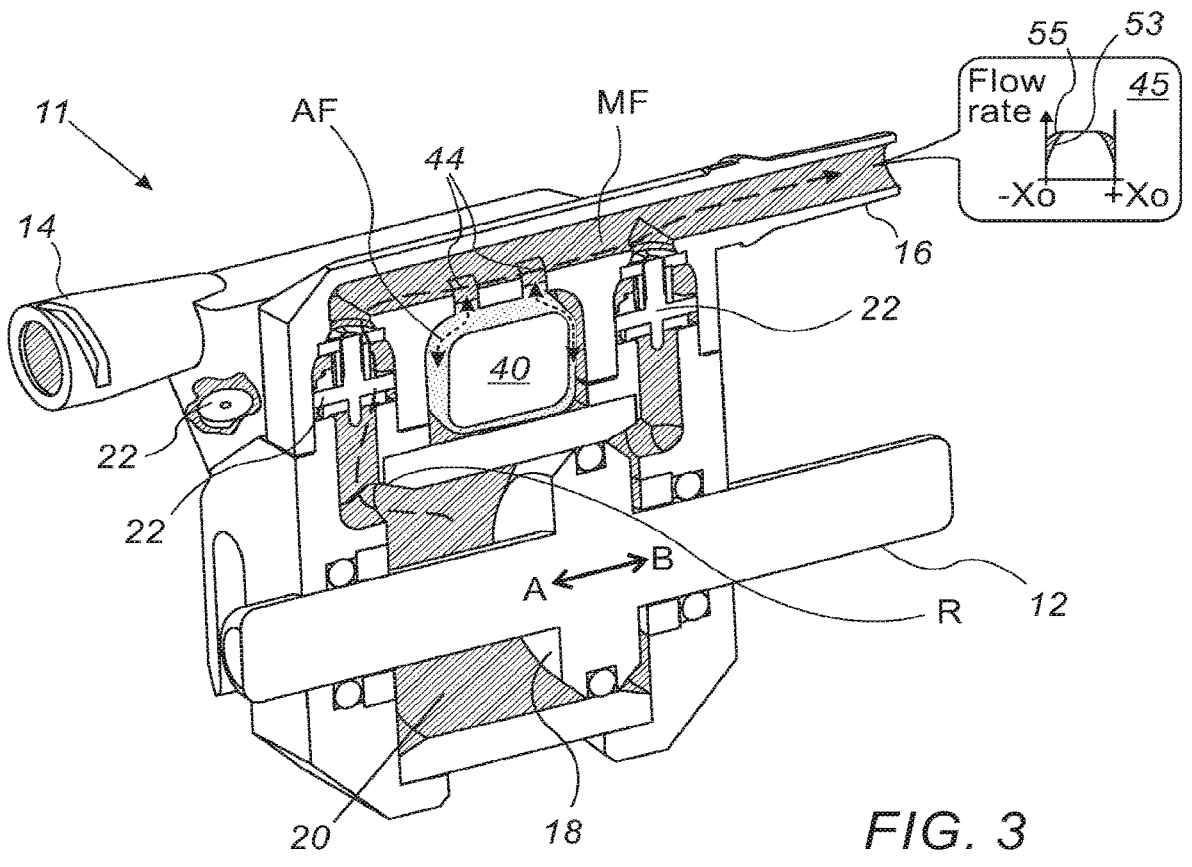
FIG. 3 is a cross-sectional view of a disposable single-piston dual-action pump part including a balloon damper, in accordance with an embodiment of the present invention.

FIG. 3 is a cross-sectional view of a disposable single-piston dual-action pump part 11 including a balloon damper 40, in accordance with an embodiment of the present invention. As seen, balloon 40 is fitted inside pump part 11 at the exit port of part 11. Pump part 11 functions as described for part 10 in FIG. 2, with the only change between parts 10 and 11 being smoothing the output flow profile of part 10 using balloon damper 40.

To establish a low and slowly varying flow rate of pump part 11, balloon 40 is configured to be compressed by surrounding fluid during the constant speed travel section of piston 18. At the piston end points, when fluid pressure drops, the balloon expands, increasing the flow rate from the lower value caused by the piston changing direction. Inset 45 shows a graph that demonstrates the more uniform flowrate 55 when using balloon 40, as compared with a flowrate 53 profile demonstrated without using balloon 40. As seen by the shaded area, towards end points $-X_0$ and $+X_0$, the output flow of the pump drops substantially unless balloon dumper 40 is used.

In some embodiment, balloon 40 has a special half-crescent cylindrical shape, which best fit an available space inside part 11, so as to maximize the volume of the balloon and by so to maximize the damping effect of balloon over pulsations in the output flow.

The example illustration shown in FIG. 3 is chosen purely for the sake of conceptual clarity. The shape of balloon 40 and the shape, location, and number of channels 44 may vary.

Reducing Pulsation in Dual-Action Reciprocating Pump

Figure 4:
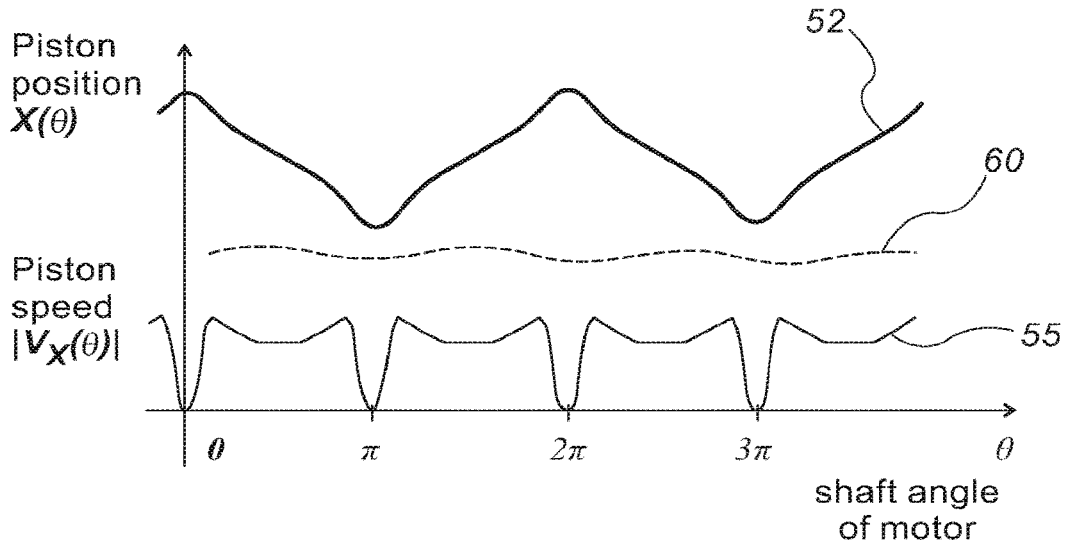
FIG. 4 is a graph describing motion of the piston of the disposable dual-action pump of FIG. 1 as a function of an angle of the rotary motor of the pumping system, in accordance with an embodiment of the present invention.

FIG. 4 is a graph describing motion of the piston of the disposable dual-action pump of FIG. 1 as a function of an angle of the rotary motor of the pumping system, in accordance with an embodiment of the present invention.

The disclosed graphs 52 and 55, are derived by a designer from a requirement for an outflow, seen as graph being be as uniform as possible.

Periodic graph 52 shows piston position as a function of shaft angle of the rotary driving motor. As seen, near turning points of piston travel (i.e., about rotary angles $\pi$, $2\pi$ . . . ), the piston position, X, depends non-linearly on the shaft angle. An underlying cause of the variable speed motion of the piston is seen in graph 55, in which the piston speed $V_X$ is increased just before and after piston speed decelerates as piston instantaneously halts at a cylinder turning end.

As noted above, a processor inside system 100 may instruct the system to vary the output flow rate, for example, by a combination of speeding up and slowing down the rotation of the motor, so as to reduce a pulsation.

Figure 5:
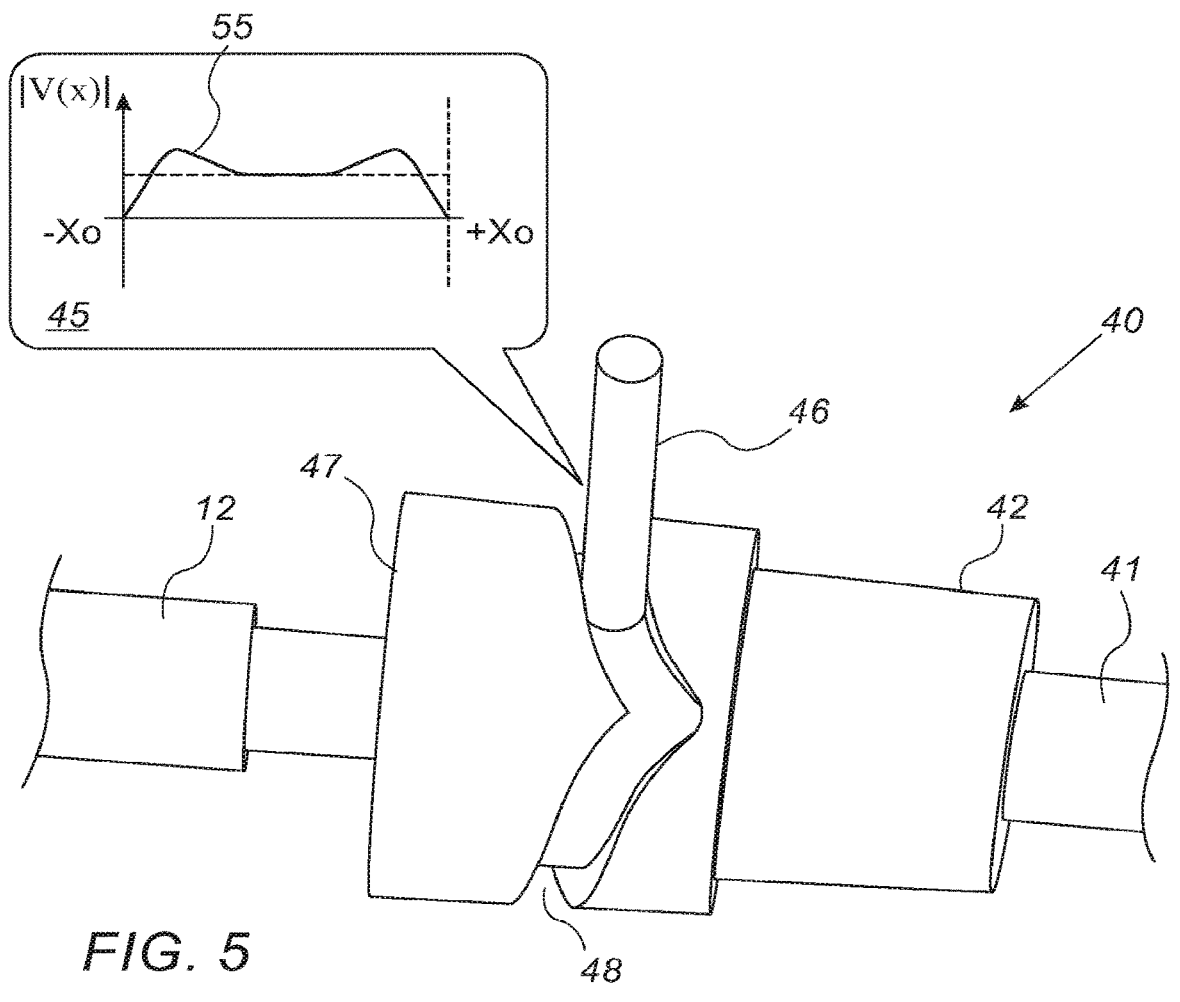
FIG. 5 is a schematic volume rendering of a mechanical smoothing mechanism, in accordance with an embodiment of the present invention.

FIG. 5 is a schematic volume rendering of mechanical smoothing mechanism 40, in accordance with an embodiment of the present invention. In some embodiments, mechanical smoothing mechanism 40 is used for achieving a desired profile of the output flow of part 10, such as profile 60.

As seen, rod 12 is coupled to a guide hub 47 having a guide channel 48. A cylinder head 42 of mechanism 40 is coupled to a rotary shaft 41 of the driving motor (not seen). Guide hub 47 is coupled to head 42 by a bar 46 that is screwed into head 42 so that bar 46 rotates with rotary shaft 41. Because of guide channel 48, guide hub 47 is not rotationally coupled to rod 12, rather element 47 moves back and forth in a variable speed motion induced by bar 46 pushing and pulling element 47 (and with it rod 12 and hence piston 18) as bar 46 moves rotationally along guide channel 48, forcing guide hub 47 to translate rod 12 along its axis in accordance with the path defined by guide channel 48.

Slit 48 profile is designed to convert the rotation of shaft 41 into the variable speed profile 55 V(X) of rod 12, seen in inset 45, as a function of the piston travel between turning ends $-X_0$ and $+X_0$ of the cylinder inside pump part 10.

The example illustration shown in FIG. 5 is chosen purely for the sake of conceptual clarity. Only elements of mechanical smoothing mechanism 40 relevant to the invention are described, whereas many other parts that mechanical smoothing mechanism 40 may include, such as screws, are omitted for simplicity.

Figure 6:
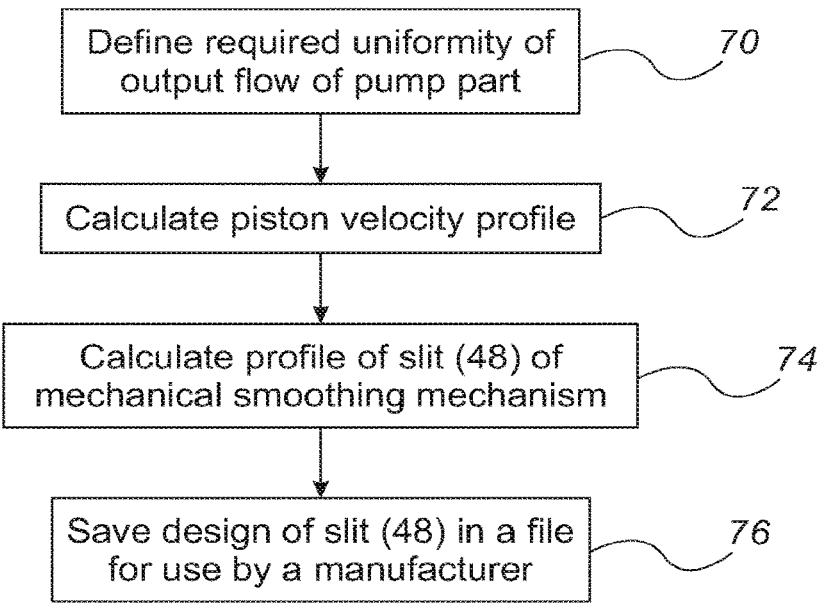
FIG. 6 is a flow chart describing a design method of portion of the mechanical smoothing mechanism of FIG. 5, in accordance with an embodiment of the present invention.

FIG. 6 is a flow chart describing a design method of the mechanical smoothing mechanism 40 of FIG. 5, in accordance with an embodiment of the present invention. The process begins with defining a required, constant as possible, output flow profile of pump part 10, at an output flow requirement step 70. Next, based on required profile of output flow provided at step 70, a designer calculates piston velocity profile 55, at a piston velocity calculation step 72. Using the velocity profile, the designer calculates a profile of guide channel (e.g., slit 48 of mechanical smoothing mechanism 40 that will produce the required output flow profile of pump part at a mechanical guide channel profile calculation step 74. Finally, the designer saves the design of mechanical smoothing mechanism 40, including of slit 48, in a file for use by a manufacturer, at a design saving step 76.

Using Silicone O-Rings in Dual Action Irrigation Pump

Figure 7:
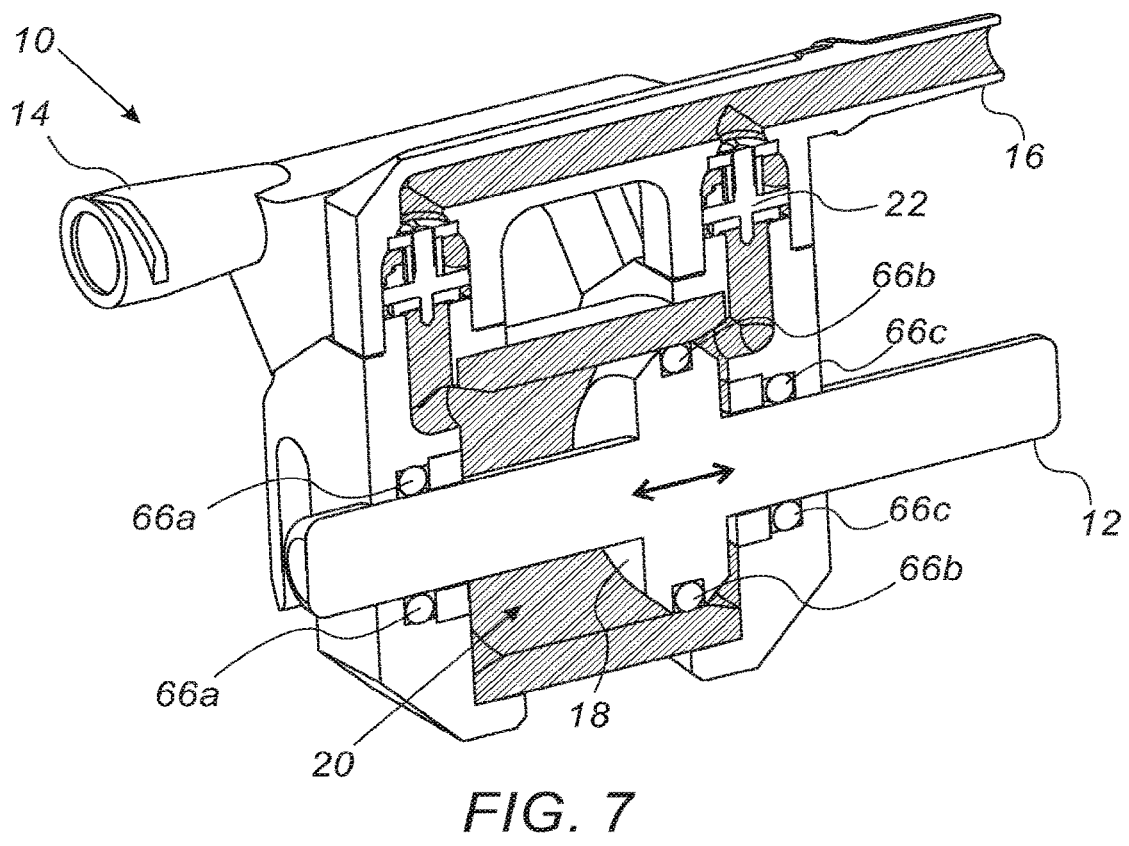
FIG. 7 is a cross-sectional view of the disposable single-piston dual-action pump part of FIG. 1 including silicone O-rings, in accordance with an embodiment of the present invention.

FIG. 7 is a cross-sectional view of the disposable single-piston dual-action pump part 10 of FIG. 1 including silicone O-rings 66, in accordance with an embodiment of the present invention. The functioning of part 10 is described in FIG. 2.

Three silicone O-rings 40 (i.e., 66a, 66b and 66c) are fitted in pump part 10 to seal piston 18 against cylinder so as to establish efficient pumping functionality and to avoid leakages as piston 18 moves bi-directionally to pump the fluid, as described below.

As seen, silicon O-rings 66a and 66c are fitted in cylinder 20 in a way that O-rings 66a and 66c prevent fluid from leaking outside of pump part 10. O-ring 66*b* is fitted over piston 18 perimeter, so as to prevent pumped fluid (i.e., fluid under pressure) from leaking around piston 18 into the volume of cylinder 20 separated by piston 18, wherein that increased volume serves for fluid intaking. As the piston reverses direction, O-ring 66*b* serves to seal against flow in the opposite direction.

The example illustration shown in FIG. 7 is chosen purely for the sake of conceptual clarity. The cross-section, location and number of silicone O-rings 66 may vary.

Manufacturing Process of the Pump Part

Figure 8:
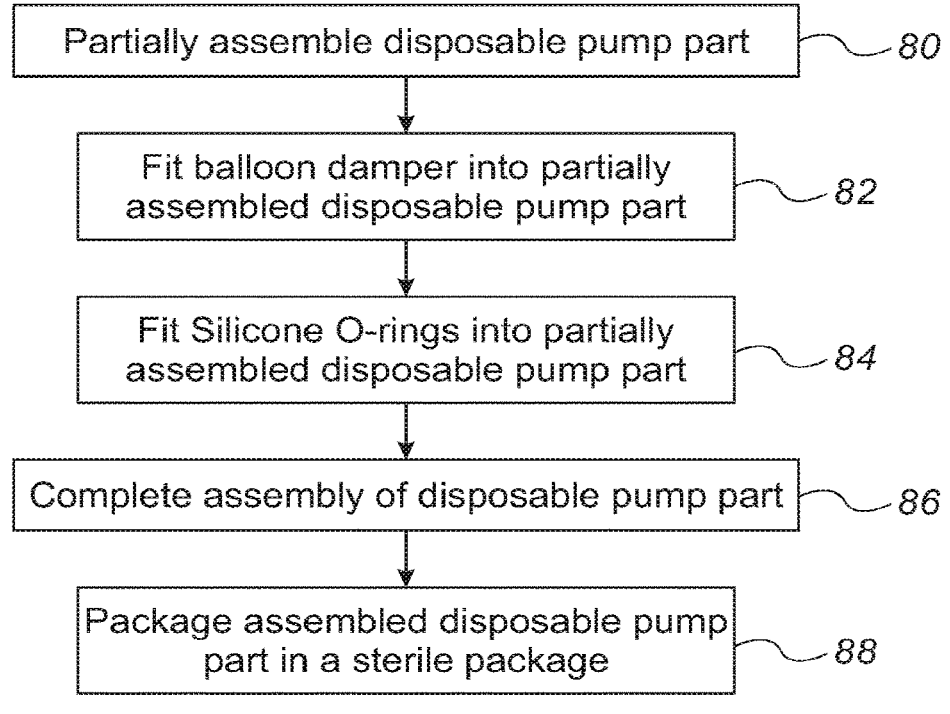
FIG. 8 is a flow chart describing a manufacturing method of the disposable single-piston dual-action pump part of FIG. 1, in accordance with an embodiment of the present invention.

FIG. 8 is a flow chart describing a manufacturing method of the disposable single-piston dual-action pump part 11 of FIG. 3, in accordance with an embodiment of the present invention.

The process begins with partially assembling disposable dual-action reciprocating pump part 11, at a pump part assembly step 80. Next, silicone O-rings 66 are fitted into the partially assembled pump part 11, at a silicone O-rings fitting step 82. Next, balloon damper 40 is fitted into the partially assembled pump part 11, at a balloon damper fitting step 84. Alternatively or additionally, the pulsation is controlled by the disclosed mechanical smoothing mechanism and/or by the processor changing the rate of rotation, as described above.

Then, the manufacturing method includes finishing the assembly of pump part 11 into the disposable dual-action reciprocating pump, at a pump full assembly step 86. Finally, the fully assembled pump part 10 is packaged in a sterile package, at a sterile packaging step 88.

The example flow-chart shown in FIG. 8 is chosen purely for the sake of conceptual clarity. Only manufacturing steps that are relevant to embodiments of the invention are shown.

Although the embodiments described herein mainly address a non-sterilizable pump part for catheter irrigation, the disclosed single-use pump part described herein can also be used in other medical applications, such as in injection of contrast agents for medical imaging and in intravenous infusion.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method of manufacturing a pump part, comprising:
    (a) partially assembling the pump part, the pump part comprising the following, and the partially assembling comprising assembling at least some of the following:
        a single piston configured and positioned to contact fluid;
        a cylinder having two ends and configured for longitudinal travel of the single piston from one end to the other end of the cylinder;

a pair of output passages, each output passage of the pair of output passages including a one-way valve and, each output passage of the pair of output passages being configured to be in fluid communication with an end of the cylinder, each output passage of the pair of output passages being in fluid communication with a different end of the cylinder relative to the other output passage;
        an output port for outputting fluid pumped by the single piston, the output port being configured to be fluidly connected to each of the output passages, each one-way valve being configured to allow the fluid to flow in one direction from the output passage to the output port; and
        a rod configured to drive the single piston and to traverse each end of the cylinder;
    (b) fitting a balloon damper including a balloon in a chamber which is in fluid communication with the output port, the chamber being in fluid communication with the output port via a pair of channels communicating from the chamber into the output port, the pair of channels being located at respective longitudinal locations that are between the pair of output passages, the balloon damper being fitted in the chamber such that it is configured to suppress a pulsation in a flow rate of the outputted fluid;
    (c) fitting a pair of gaskets, each gasket of the pair of gaskets being fitted such that it is positioned between the rod and the respective end of the cylinder, each gasket of the pair of gaskets being fitted such that it is configured to seal the respective end of the cylinder;
    (d) completing assembly of the pump part.

2. The method according to claim 1, wherein the fitting the balloon damper comprises accepting, by the balloon damper, a shape of the chamber into which the balloon is fitted.

3. The method according to claim 1, further comprising packaging the assembled pump part in a sterile package.

4. The method according to claim 1, the fitting the balloon damper comprising fitting the balloon in the chamber such that it is configured to suppress the pulsation in the flow rate of the outputted fluid by the balloon damper returning, when the output flow rate is reduced, to an uncompressed volume and pushing a pulled fluid through the output port.

5. The method according to claim 1, the partially assembling the pump part or the completing assembly of the pump part comprising providing the single piston with a seal configured to prohibit fluid flow between the two ends of the cylinder.

6. The method according to claim 5, the seal comprising silicone.

7. The method according to claim 1, the partially assembling the pump part or the completing assembly of the pump part comprising axially coupling the single piston to the rod such that the rod is configured to reciprocate the single piston in two directions inside the cylinder, at least a portion of the rod being configured and positioned to contact the fluid.

8. The method according to claim 7, the partially assembling the pump part or the completing assembly of the pump part comprising rotatably coupling the rod to a shaft that is configured to rotate, the shaft defining a reciprocation channel positioned along a periphery of the shaft, the reciprocation channel being configured to follow a stationary guide upon rotation of the shaft and thereby reciprocate the rod and the single piston.

9. The method according to claim 8, the reciprocation channel being configured to accelerate the single piston just before the single piston reaches a cylinder end.

10. The method according to claim 1, the partially assembling the pump part or the completing assembly of the pump part further comprising providing an input port separated from the pair of output passages by a pair of non-return valves, each non-return valve being connected to an output passage of the pair of output passages, each non-return valve being configured to allow the fluid to flow in one direction from the input port to the respective output passage.

11. The method according to claim 1, the partially assembling the pump part or the completing assembly of the pump part further comprising providing a processor, the processor being configured to control a speed of the single piston.

12. A method of manufacturing a pump part, comprising:
(a) partially assembling the pump part, the pump part comprising the following, and the partially assembling comprising assembling at least some of the following:
a cylinder having two ends defined by a cylinder body;
a single piston axially coupled to a rod, the rod being configured to reciprocate the single piston in two directions inside the cylinder and to traverse each end of the cylinder, at least a portion of the rod being configured and positioned to contact fluid, the rod having a first end and a second end;
a pair of output passages, each output passage of the pair of output passages being located at a respective longitudinal position that is between an input port and an output port, each output passage of the pair of output passages including a one way valve, each output passage of the pair of output passages being configured to be in fluid communication with a respective end of the cylinder, each output passage of the pair of output passages being in fluid communication with a different end of the cylinder relative to the other output passage;
the input port for inputting fluid to be pumped by the single piston; and
the output port for outputting fluid pumped by the single piston, the single piston being configured to pump fluid into the output port while traveling in either direction of the two directions;
(b) fitting a balloon damper including a balloon in a chamber which is in fluid communication with the output port, the balloon damper being fitted in the chamber such that it is configured to suppress a pulsation in a flow rate of the outputted fluid; and
(c) fitting a pair of seal members, each seal member of the pair of seal members being fitted such that it is positioned between the rod and the respective end of the cylinder, each seal member of the pair of seal members being configured to seal the respective end of the cylinder, the pair of seal members being positioned such that the first and second ends of the rod extend past the seal members and protrude outwardly from the cylinder body; and
(d) completing assembly of the pump part.

13. The method according to claim 12, wherein the fitting the balloon damper comprises accepting, by the balloon damper, a shape of the chamber into which the balloon is fitted.

14. The method according to claim 12, further comprising packaging the assembled pump part in a sterile package.

15. The method according to claim 12, the partially assembling the pump part or the completing assembly of the pump part further comprising rotatably coupling the rod to a shaft that is configured to rotate, the shaft defining a reciprocation channel positioned along a periphery of the shaft, the reciprocation channel being configured to follow a stationary guide upon rotation of the shaft and thereby reciprocate the rod and the single piston.

16. A method of manufacturing a pump part, comprising:
(a) partially assembling the pump part, the pump part comprising the following, and the partially assembling comprising assembling at least some of the following:
a single piston configured and positioned to contact fluid;
a cylinder having two ends and configured for longitudinal travel of the single piston from one end to the other end of the cylinder;
a pair of output passages located at respective longitudinal positions that are between an input port and an output port, each output passage of the pair of output passages including a one-way valve, each output passage of the pair of output passages being configured to be in fluid communication with a respective end of the cylinder, each output passage of the pair of output passages being in fluid communication with a different end of the cylinder relative to the other output passage;
the input port for inputting fluid to be pumped by the single piston; and
the output port for outputting fluid pumped by the single piston, the output port being configured to be fluidly connected to each of the output passages, each one-way valve being configured to allow the fluid to flow in one direction from the output passage to the output port;
(b) fitting a balloon damper including a balloon in a chamber which is in fluid communication with the output port via a first channel and via a second channel, the balloon damper being fitted in the chamber such that it is configured to suppress a pulsation in a flow rate of the outputted fluid, the first channel and the second channel being located at respective longitudinal positions that are between the output passages; and
(c) completing assembly of the pump part.

17. The method according to claim 16, wherein the fitting the balloon damper comprises accepting, by the balloon damper, a shape of the chamber into which the balloon is fitted.

18. The method according to claim 16, further comprising packaging the assembled pump part in a sterile package.

* * * * *